United States Patent
Baek et al.

(10) Patent No.: US 9,726,620 B2
(45) Date of Patent: Aug. 8, 2017

(54) COMPUTED TOMOGRAPHY SYSTEM INCLUDING ROTATABLE COLLIMATOR

(71) Applicants: SAMSUNG ELECTRONICS CO., LTD., Suwon-si (KR); INDUSTRY-ACADEMIC COOPERATION FOUNDATION, YONSEI UNIVERSITY, Seoul (KR)

(72) Inventors: Jong-duk Baek, Incheon (KR); Chang-woo Lee, Yongin-si (KR); Jae-sung Lee, Seoul (KR); Young-jun Ko, Seoul (KR)

(73) Assignees: SAMSUNG ELECTRONICS CO., LTD., Suwon-si (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 204 days.

(21) Appl. No.: 14/323,110

(22) Filed: Jul. 3, 2014

(65) Prior Publication Data

US 2015/0016587 A1    Jan. 15, 2015

(30) Foreign Application Priority Data

Jul. 12, 2013 (KR) .......... 10-2013-0082463

(51) Int. Cl.
*G01N 23/04* (2006.01)
*G21K 1/02* (2006.01)
(Continued)

(52) U.S. Cl.
CPC .......... *G01N 23/046* (2013.01); *A61B 6/032* (2013.01); *A61B 6/06* (2013.01); *G21K 1/02* (2013.01);
(Continued)

(58) Field of Classification Search
CPC .......... A61B 6/03; A61B 6/032; A61B 6/035; A61B 6/06; A61B 6/542; A61B 6/4085; G21K 1/02; G21K 1/025; G01N 23/046
See application file for complete search history.

(56) References Cited

U.S. PATENT DOCUMENTS

| | | | | |
|---|---|---|---|---|
| 6,556,657 B1 * | 4/2003 | Tybinkowski | ........... | G21K 1/02 378/147 |
| 7,532,704 B2 * | 5/2009 | Hempel | ................. | A61B 6/032 378/145 |

(Continued)

FOREIGN PATENT DOCUMENTS

| | | |
|---|---|---|
| JP | 2005-185574 A | 7/2005 |
| KR | 10-2006-0050407 A | 5/2006 |

(Continued)

OTHER PUBLICATIONS

Communication dated Oct. 17, 2014 issued by the International Searching Authority in counterpart International Application No. PCT/KR2014/006261 (PCT/ISA/220/210/237).

*Primary Examiner* — Hoon Song
(74) *Attorney, Agent, or Firm* — Sughrue Mion, PLLC

(57) ABSTRACT

Disclosed is a computed tomography (CT) system which includes a rotatable collimator. The CT system includes a gantry. The gantry includes an X-ray source that generates X-rays, a collimator that is provided inside the X-ray source to be rotatable and that limits an irradiation area of the X-rays generated by the X-ray source, and an X-ray detector that is provided at a side portion of the X-ray source.

18 Claims, 4 Drawing Sheets

(51) Int. Cl.
*A61B 6/03* (2006.01)
*A61B 6/06* (2006.01)
A61B 6/04 (2006.01)
A61B 6/00 (2006.01)

(52) U.S. Cl.
CPC ........... *A61B 6/0407* (2013.01); *A61B 6/4007* (2013.01); *A61B 6/4266* (2013.01)

(56) References Cited

U.S. PATENT DOCUMENTS

| | | |
|---|---|---|
| 2004/0028181 A1 | 2/2004 | Charles, Jr. et al. |
| 2006/0039536 A1 | 2/2006 | Nishide et al. |
| 2006/0159221 A1* | 7/2006 | Popescu ................. A61B 6/032 378/10 |
| 2007/0116173 A1 | 5/2007 | Arenson et al. |
| 2010/0246752 A1 | 9/2010 | Heuscher et al. |
| 2011/0002439 A1 | 1/2011 | Zhang |
| 2011/0113645 A1 | 5/2011 | Huisstede et al. |
| 2012/0128120 A1 | 5/2012 | De Man et al. |

FOREIGN PATENT DOCUMENTS

| | | |
|---|---|---|
| KR | 10-2011-0028458 A | 3/2011 |
| KR | 10-1076319 B1 | 10/2011 |

\* cited by examiner

COMPUTED TOMOGRAPHY SYSTEM INCLUDING ROTATABLE COLLIMATOR

CROSS-REFERENCE TO RELATED APPLICATIONS

This application claims priority from Korean Patent Application No. 10-2013-0082463, filed on Jul. 12, 2013, in the Korean Intellectual Property Office, the disclosure of which is incorporated herein by reference in its entirety.

BACKGROUND

1. Field

One or more exemplary embodiments relates to a computed tomography (CT) system, and more particularly, to a CT system including a rotatable collimator.

2. Description of the Related Art

A CT system is an apparatus that irradiates X-rays on an object at several angles, measures the X-rays passing through the object, reconstructs an absorption value of a cross-sectional surface of the object, and displays the reconfigured absorption value as an image.

In general X-ray photographs, a three-dimensional (3D) image of an object is displayed on a two-dimensional (2D) film. However, the CT system displays a 3D image of a selected cross-sectional surface, and thus, may be used to accurately diagnose various cases that are difficult to diagnose with a general X-ray photograph. The CT system examines an object nondestructively and safely, and thus is widely used for finding an internal shape or density of an object in both industry and medical fields.

In CT system technology, research is being conducted into reducing a time which is required for acquiring an image and for reducing an amount of X-rays to which a patient is exposed. Therefore, the CT system technology is continuously advancing.

SUMMARY

One or more exemplary embodiments includes a CT system including a rotatable collimator.

Additional aspects will be set forth in part in the description which follows and, in part, will be apparent from the description, or may be learned by practice of the presented exemplary embodiments.

According to one or more exemplary embodiments, a CT system including a rotatable collimator includes: a gantry that includes a cylindrical opening area which is formed at a central portion of the gantry; and an object table configured to move an object into an opening area of the gantry, the object being an examination target, wherein the gantry includes: an X-ray source configured to generate X-rays; a collimator that is provided inside the X-ray source to be rotatable, and configured to limit an irradiation area of the X-rays generated by the X-ray source; and an X-ray detector that is provided at a side portion of the X-ray source.

From among the X-ray source, the collimator, and the X-ray detector, only the collimator may be rotatable, and each of the X-ray source and the X-ray detector may be fixed so as not to rotate.

The X-ray source may be provided at each of a first side portion and a second side portion of the X-ray detector.

Each of the X-ray source, the collimator, and the X-ray detector may be provided in a ring type.

The X-ray detector may include a plurality of detectors.

Each of the plurality of detectors included in the X-ray detector may include at least one from among a solid state detector (SSD), a Xe-gas type detector, and a photon-counting detector.

The collimator may include a plurality of slits that are configured to limit an irradiation area of X-rays which are irradiated from the X-ray source toward the opening area of the gantry.

A rotation speed of the collimator may correspond to a periodicity which is less than or equal to 0.1 seconds per revolution.

According to one or more exemplary embodiments, a CT system including a rotatable collimator includes: a gantry that includes: an X-ray source configured to generate X-rays; a collimator that is provided inside the X-ray source to be rotatable; and an X-ray detector that is provided at a side portion of the X-ray source; and a controller configured to drive the gantry when an object is located in the gantry.

The CT system may further include an image processor configured to analyze information which relates to X-rays which are detected by the X-ray detector in order to acquire 3D information which relates to the object.

BRIEF DESCRIPTION OF THE DRAWINGS

These and/or other aspects will become apparent and more readily appreciated from the following description of the exemplary embodiments, taken in conjunction with the accompanying drawings of which.

DETAILED DESCRIPTION

Figure 1:
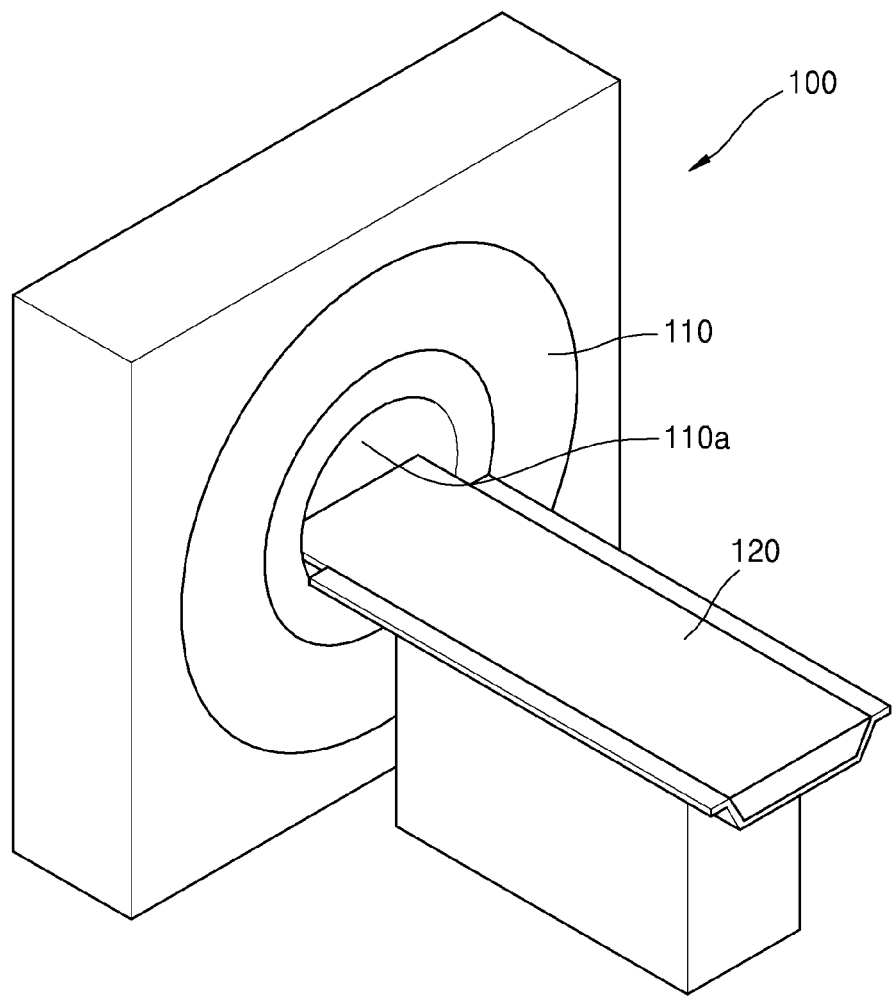
FIG. 1 is a view which schematically illustrates an external appearance of a CT system, according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, in order to explain aspects of the present disclosure.

Hereinafter, a power semiconductor device according to an exemplary embodiment will be described in detail with reference to the accompanying drawings. For reference, like reference numerals refer to like elements throughout, and elements having the same name may be formed of the same material. In the drawings, the size of each element may be exaggerated for clarity and convenience of description.

The term "object" used herein may include a person, an animal, a part of the person, or a part of the animal. For example, an object may include an organ such as any one or more of a liver, a heart, a womb, a brain, breasts, an abdomen, and/or the like, or a blood vessel, but is not limited thereto.

FIG. 1 is a view which schematically illustrates an external appearance of a CT system, according to an exemplary embodiment.

Referring to FIG. 1, a CT system 100 according to an exemplary embodiment includes a gantry 110, which includes a cylindrical opening area 110a formed at a central portion of the gantry 110, and an object table 120 on which an object (such as, for example, an examination target) is located so as to facilitate a movement of the object into the opening area 110a of the gantry 110.

Figure 2A:
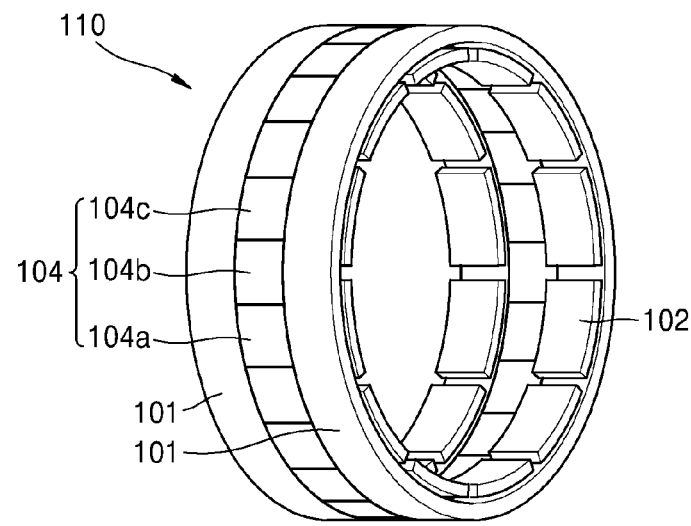
FIG. 2A is a view which illustrates a configuration of a gantry of the CT system, according to an exemplary embodiment.
Figure 2B:
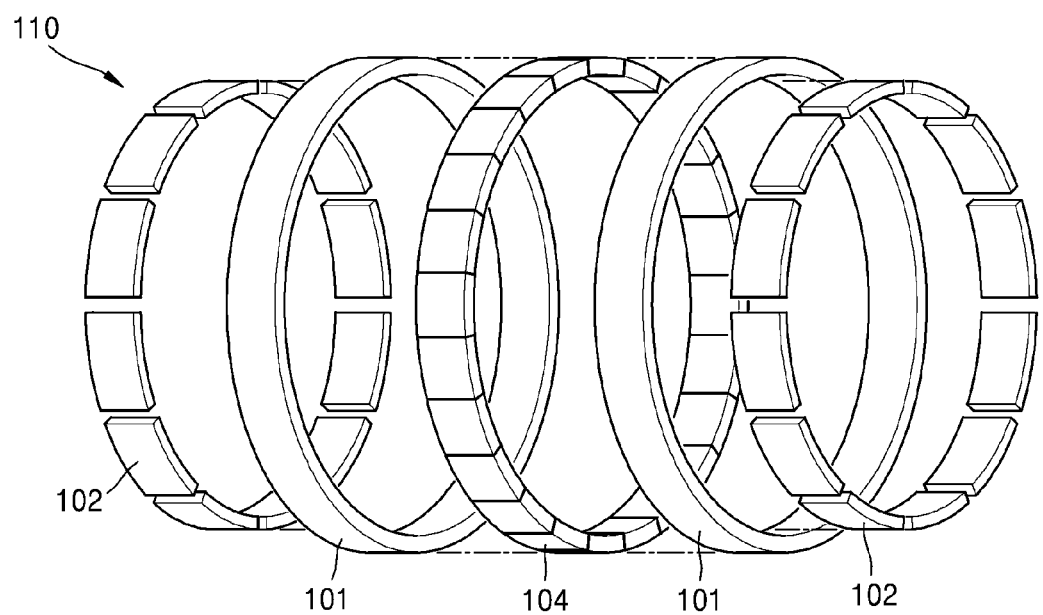
FIG. 2B is an exploded perspective view which illustrates the gantry of the CT system of FIG. 2A.

FIG. 2A is a view which illustrates a configuration of a gantry of the CT system, according to an exemplary embodiment. FIG. 2B is an exploded perspective view which illustrates the gantry of the CT system of FIG. 2A.

Referring to FIGS. 1, 2A, and 2B, the gantry 110 may include an X-ray source 101 that is configured to generate X-rays, a collimator 102 that is provided inside the X-ray source 101 and that is configured to limit an irradiation area of the X-rays generated by the X-ray source 101, and an X-ray detector 104 that is configured to detect the X-rays which are generated by the X-ray source 101, which X-rays are irradiated toward an object through the collimator 102, and propagate through the object.

The X-ray source 101 is an element that is configured to irradiate X-rays toward an object (such as, for example, an examination target) which is located on the object table 120 and moved into the opening area 110a of the gantry 110. The X-ray source 101 may include any one or more of various types of X-ray generation structures, and may include a plurality of electron emission sources. The X-ray source 101 may be disposed in order for an electron gun to irradiate the X-rays toward the opening area 110a of the gantry 110, and may be used with no restriction when the X-ray source is under a condition which enables generation of the X-rays.

For example, the X-ray source 101 may include an electron emission source configured for emitting electrons and an anode electrode that emits X-rays which are generated as a result of at least one collision of the emitted electrons. The X-ray source 101 may include a cathode electrode and the electron emission source may be disposed on the cathode electrode, and the cathode electrode may be configured to emit electrons. The cathode electrode may be formed of at least one metal, such as any one or more of titanium (Ti), platinum (Pt), ruthenium (Ru), gold (Au), silver (Ag), molybdenum (Mo), aluminum (Al), tungsten (W), or copper (Cu), and/or a metal compound such as indium-tin-oxide (ITO), aluminum-zinc-oxide (AZO), indium-zinc-oxide (IZO), SnO2, or In2O3. The electron emission source may be formed of a material that emits electrons, and for example, may be formed of any one or more of a metal, silicon, oxide, diamond, diamond-like carbon (DLC), a carbon compound, a nitrogen compound, a carbon nano tube, and/or the like.

The X-ray source 101 may be provided in a ring type, and may include a plurality of electron emission sources. A position of the X-ray source 101 may be partially changed when the gantry 110 is being driven, but the position of the X-ray source 101 may be fixed so as not to rotate.

The collimator 102 may be provided inside the X-ray source 101, and the collimator 102 may be provided in a ring type, which type may be based on an internal type of the X-ray source 101. The collimator 102 may include a plurality of slits which are configured to limit an irradiation area of X-rays which are irradiated from the X-ray source 101 toward the opening area 110a of the gantry 110. A respective width of each of the plurality of slits included in the collimator 102 may be adjustable. Unlike the X-ray source 101, when the gantry 110 is being driven, the collimator 102 may rotate around the opening area 110a with respect to a central portion of the opening area 110a of the gantry 110.

The X-ray detector 104 may be provided at a side portion of the X-ray source 101. The X-ray detector 104 may include a plurality of detectors 104a, 104b, 104c, . . . which are configured to detect X-rays which are irradiated onto an object through the slits of the collimator 101, and which propagate through the object. The X-ray detector 104 may use any one or more of various types of detectors, and is not limited thereto. For example, the X-ray detector 104 may use any one or more of a solid state detector (SSD), a xenon (Xe)-gas type detector, and/or a photon-counting detector. When the CT system according to an exemplary embodiment uses the photon-counting detector, a pulse pile-up problem that may be caused by a lower counting rate in a multi energy CT system is physically resolved. The X-ray detector 104 may be provided at a side portion of the X-ray source 101 in the same ring type as the X-ray source 101. A position of the X-ray detector 104 may be partially changed when the gantry 110 is being driven, but the position of the X-ray detector 104 may be fixed so as not to rotate.

In FIGS. 2A and 2B, the X-ray source 101 is illustrated as being provided in a ring type at each of two opposite side portions of the X-ray detector 104. However, this is merely an example. As another example, the X-ray source 101 may be provided at only one side portion of the X-ray detector 104, and moreover, the X-ray detector 104 and the X-ray source 101 may be additionally provided.

Figure 3A:
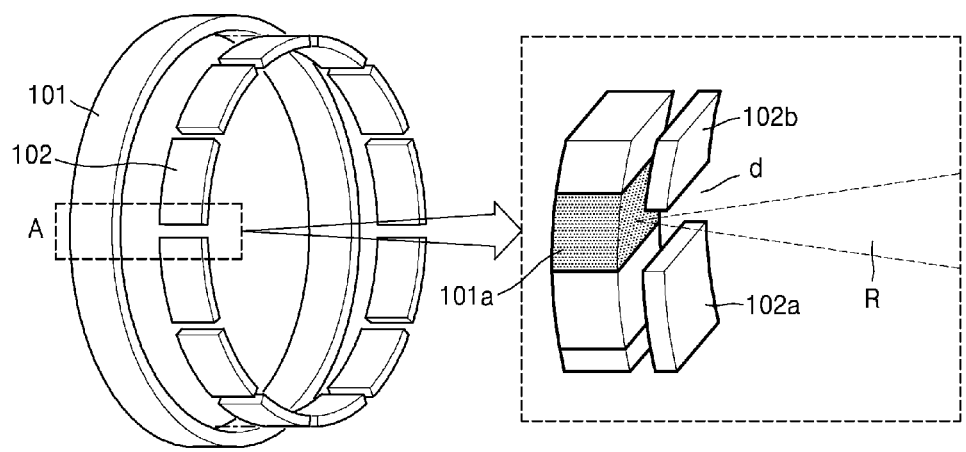
FIG. 3A is a view which illustrates a portion of each of an X-ray source and a collimator of the gantry in the CT system, according to an exemplary embodiment.
Figure 3B:
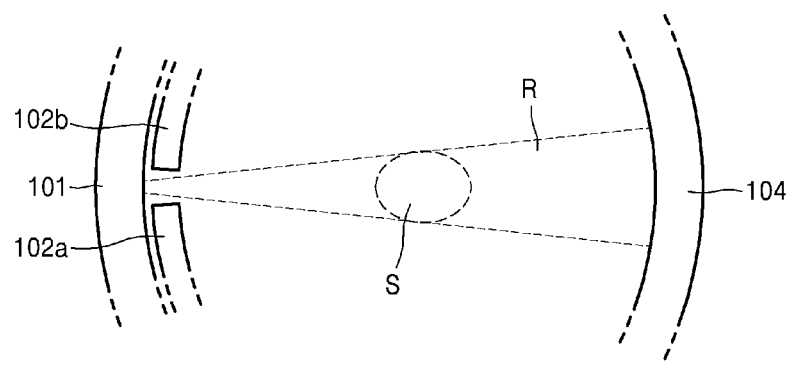
FIG. 3B is a view which illustrates that X-rays generated by the X-ray source of the gantry propagate through an object and are detected by a detector in the CT system, according to an exemplary embodiment.

FIG. 3A is a view which illustrates a portion of each of the X-ray source and the collimator of the gantry in the CT system, according to an exemplary embodiment. FIG. 3B is a view which illustrates that X-rays which are generated by the X-ray source of the gantry propagate through an object S and are then detected by a detector in the CT system, according to an exemplary embodiment.

Referring to FIGS. 1, 3A, and 3B, when the CT system according to an exemplary embodiment is being driven, as illustrated with respect to an area A, X-rays R which are emitted from the X-ray source 101 of the gantry 110 are irradiated toward the opening area 101a with an object S located therein. A beam width of the X-rays R may be determined by a slit d of the collimator 102 which is disposed inside the X-ray source 101. A width of the slit d may be controlled by a plurality of collimators 102a and 102b which are respectively disposed at both sides of the slit d so as to cause the X-rays R generated by the X-ray source 101a to have a narrow line width, thereby reducing an influence of scatter. The X-rays which propagate through the object S may be detected by the X-ray detector 104, thereby enabling image information which relates to the object S to be acquired. The slit d is exemplarily illustrated in the drawing, and a number of the slits d formed at the ring type of collimator 102 may be in a range of several hundreds or thousands, with no limitation.

In the CT system according to an exemplary embodiment, the ring type X-ray source 101 and the X-ray detector 104 of the gantry 110 are provided so as not to rotate, and only the collimator 102 of the gantry 110 may rotate. The collimator 102 has a relatively lighter weight than the X-ray source 101 and the X-ray detector 104, and may be configured to rotate at a high speed. For example, the maximum rotation speed of the collimator 102 may correspond to a periodicity which is less than or equal to 0.1 seconds per revolution. Therefore, a rotation speed is likely to be faster in a case of rotating only the collimator 102 than in a case of rotating the entire gantry 110. In this aspect, by rotating only the collimator 102 of the gantry 110, a time in which is required for acquiring a 3D image of the object S is reduced, and an amount of X-rays to which the object S is exposed is reduced.

Figure 4:
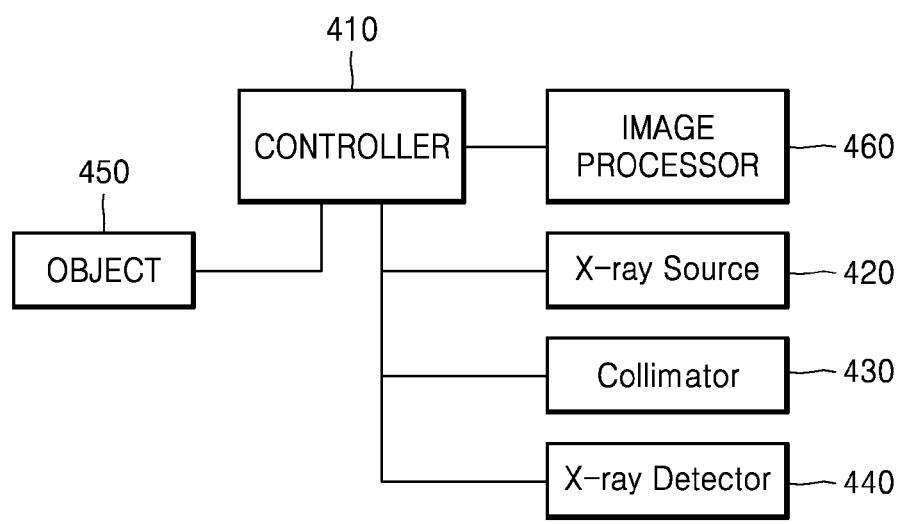
FIG. 4 is a block diagram which illustrates a configuration of the CT system, according to an exemplary embodiment.

FIG. 4 is a block diagram which illustrates a configuration of the CT system, according to an exemplary embodiment.

Referring to FIGS. 1 and 4, the CT system according to an exemplary embodiment may be controlled by a controller 410. An object 450 is located on the object table 120, and then the controller 410 drives the object table 120 and performs control in order for the object 450 to be located at a predetermined position of the opening area 110a of the gantry 110.

The controller 410 may be configured to drive a driver of the gantry 110, and to control each of an X-ray source 420, a collimator 430, and an X-ray detector 440. For example, the controller 410 may be configured to drive the gantry 110, to precisely control a position of each of the X-ray source 420, the collimator 430, and the X-ray detector 440, to control a rotation speed of the collimator 430, and to adjust a width of a slit of the collimator 430.

X-rays which are emitted from the X-ray source 420 are irradiated toward the object 450 through the collimator 430 and propagate through the object 450, and the X-ray detector 440 detects X-ray information. The X-ray information undergoes an image analysis operation that is performed by an image processor 460 in accordance with a control which is executed by the controller 410, and thus, 3D image information which relates to the object 450 is obtained. The image information which relates to the object 450 may be displayed by a display which is connected to the CT system.

The CT system according to an exemplary embodiment may include a rotatable collimator.

In the CT system according to an exemplary embodiment, in driving, only the collimator may rotate, and the X-ray source and the X-ray detector may be fixed so as not to rotate.

In the CT system according to an exemplary embodiment, because only the collimator may rotate, a rotation speed is more enhanced than a case in which the entire gantry rotates.

The CT system according to an exemplary embodiment shortens a time required for acquiring a 3D image of an object, and greatly reduces an amount of X-rays to which the object is exposed.

The CT system according to an exemplary embodiment may include a CT apparatus which is configured for use in conjunction with a cone type of beam board.

It should be understood that the exemplary embodiments described herein should be considered in a descriptive sense only and not for purposes of limitation. Descriptions of features or aspects within each exemplary embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A computed tomography (CT) system, comprising:
a gantry that includes a cylindrical opening area which is formed at a central portion of the gantry; and
an object table configured to move an object into an opening area of the gantry, the object being an examination target,
wherein the gantry includes:
an X-ray source configured to generate X-rays;
a collimator that is provided inside the X-ray source to be rotatable, and configured to limit an irradiation area of the X-rays generated by the X-ray source; and
an X-ray detector that is provided at a side portion of the X-ray source,
and wherein the X-ray source is directly provided in a ring type at each of two opposite side portions of the X-ray detector.

2. The CT system of claim 1, wherein from among the X-ray source, the collimator, and the X-ray detector, only the collimator is rotatable, and each of the X-ray source and the X-ray detector is fixed so as not to rotate.

3. The CT system of claim 1, wherein the collimator is provided in a ring type.

4. The CT system of claim 1, wherein the X-ray detector includes a plurality of detectors.

5. The CT system of claim 4, wherein each of the plurality of detectors included in the X-ray detector includes at least one from among a solid state detector (SSD), a Xe-gas type detector, and a photon-counting detector.

6. The CT system of claim 1, wherein the collimator includes a plurality of slits that are configured to limit an irradiation area of X-rays which are irradiated from the X-ray source toward the opening area of the gantry.

7. The CT system of claim 6, wherein a rotation speed of the collimator corresponds to a periodicity which is less than or equal to 0.1 seconds per revolution.

8. A computed tomography (CT) system, comprising:
a gantry that includes: an X-ray source configured to generate X-rays; a collimator that is provided inside the X-ray source to be rotatable; and an X-ray detector that is provided at a side portion of the X-ray source; and
a controller configured to drive the gantry when an object is located in the gantry,
wherein the X-ray source is directly provided in a ring type at each of two opposite side portions of the X-ray detector.

9. The CT system of claim 8, wherein when driving the gantry, from among the X-ray source, the collimator, and the X-ray detector of the gantry, only the collimator is rotatable, and each of the X-ray source and the X-ray detector is fixed so as not to rotate.

10. The CT system of claim 8, further comprising an image processor configured to analyze information which relates to X-rays which are detected by the X-ray detector in order to acquire three-dimensional (3D) information which relates to the object.

11. The CT system of claim 8, wherein the collimator is provided in a ring type.

12. The CT system of claim 8, wherein the collimator includes a plurality of slits that are configured to limit an irradiation area of X-rays which are irradiated from the X-ray source toward an opening area of the gantry.

13. The CT system of claim 8, wherein a rotation speed of the collimator corresponds to a periodicity which is less than or equal to 0.1 seconds per revolution.

14. A method for obtaining an image by using a computed tomography (CT) system, the system including a gantry that includes a cylindrical opening area which is formed at a central portion of the gantry and an object table configured to move an object into the opening area of the gantry, the object being an examination target, the gantry including:

an X-ray source;

a collimator that is provided inside the X-ray source to be rotatable; and an X-ray detector that is provided at a first side portion of the X-ray source, wherein the X-ray source is directly provided in a ring type at each of two opposite side portions of the X-ray detector, and the method comprising:

generating, by the X-ray source, X-rays;

collimating, by the collimator, the generated X-rays so as to limit an irradiation area of the generated X-rays;

detecting, by the X-ray detector, the collimated X-rays which have propagated through the object; and obtaining the image by executing at least one image processing operation upon the detected X-rays.

15. The method of claim 14, further comprising fixing each of the X-ray source and the X-ray detector so as not to rotate.

16. The method of claim 14, wherein the X-ray detector includes a plurality of detectors, wherein each of the plurality of detectors includes at least one from among a solid state detector (SSD), a Xe-gas type detector, and a photon-counting detector.

17. The method of claim 14, wherein the collimator includes a plurality of slits, wherein each of the plurality of slits is configured to limit an irradiation area of a respective portion of the generated X-rays.

18. The method of claim 14, wherein the collimating comprises rotating the collimator at a rotation speed which corresponds to a periodicity which is less than or equal to 0.1 seconds per revolution.

* * * * *